United States Patent [19]

Fujishima et al.

[11] Patent Number: 5,731,184
[45] Date of Patent: Mar. 24, 1998

[54] PROCESS FOR PRODUCING N-ACETYL-D-GLUCOSAMINE DEACETYLASE

[75] Inventors: Shizu Fujishima; Naoko Yamano, both of Ikeda; Akihiko Maruyama; Takanori Higashihara, both of Tsukuba, all of Japan

[73] Assignee: Agency of Industrial Science & Technology, Tokyo, Japan

[21] Appl. No.: 609,107

[22] Filed: Feb. 29, 1996

[30] Foreign Application Priority Data

Mar. 13, 1995 [JP] Japan ................................. 7-081988

[51] Int. Cl.$^6$ ............................................. C12N 9/14
[52] U.S. Cl. ............................................. 435/195; 435/70.1
[58] Field of Search ............................ 435/195, 70.1

*Primary Examiner*—Leon B. Lankford, Jr.
*Attorney, Agent, or Firm*—Nikaido, Marmelstein, Murray & Oram LLP

[57] ABSTRACT

A process for producing N-acetyl-D-glucosamine deacetylase which comprises incubating a microorganism belonging to the genus Alteromonas and recovering N-acetyl-D-glucosamine deacetylase from the culture thus obtained.

1 Claim, 1 Drawing Sheet

PROCESS FOR PRODUCING N-ACETYL-D-GLUCOSAMINE DEACETYLASE

BACKGROUND OF THE INVENTION

This invention relates to an advantageous process for producing N-acetyl-D-glucosamine deacetylase. The enzyme obtained by the present invention, namely, N-acetyl-D-glucosamine deacetylase per se is important as a drug. Moreover, it is usable as an enzyme in the production of D-glucosamine which is a material useful in the fields of drugs, industry, agriculture and foods. D-Glucosamine represented by the following chemical structural formula is a useful substance which has recently attracted considerable attention particularly as a starting material in the production of glucosaminooligosaccharides having physiological activities such as antimicrobial and antitumor activities:

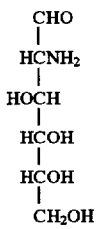

N-Acetyl-D-glucosamine deacetylase is an enzyme which acts on the acetamido group of N-acetyl-D-glucosamine represented by the following formula to thereby form D-glucosamine:

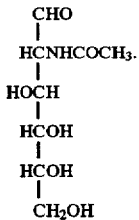

The conventional method for producing D-glucosamine comprises hydrolyzing chitin and chemically deacetylating the N-acetyl-D-glucosamine thus obtained. Conc. alkalis and mineral acids are employed in the hydrolysis.

In the above-mentioned method with the use of conc. alkalis and mineral acids, however, other necessary bonds are also cleaved simultaneously with the deacetylation, which lowers the yield of the target D-glucosamine. This method suffers from another disadvantage that the treatment of the acids and alkalis employed costs a great deal.

There has been proposed another method for the deacetylation of N-acetyl-D-glucosamine by using an enzyme (for example, deacetylase) which is expected to act exclusively on N-acetyl-D-glucosamine under mild conditions without forming any side-products. However no finding has been published so far on N-acetyl-D-glucosamine deacetylase except a report relating to the formation of this enzyme by a bacterium belonging to the genus Vibrio. Namely, there has been established no industrially usable technique for producing N-acetyl-D-glucosamine deacetylase.

SUMMARY OF THE INVENTION

The present inventors have conducted extensive studies in order to overcome the problems encountering in the conventional methods. As a result, they have successfully found that a microorganism belonging to the genus Alteromonas inductively produces a large amount of N-acetyl-D-glucosamine deacetylase, thus completing the present invention.

Accordingly, an object of the present invention is to provide an industrially advantageous process for producing N-acetyl-D-glucosamine deacetylase which is useful in the production of D-glucosamine.

To achieve this object, the process for producing N-acetyl-D-glucosamine deacetylase of the present invention comprises incubating a microorganism which belongs to the genus Alteromonas and is capable of producing N-acetyl-D-glucosamine deacetylase and recovering N-acetyl-D-glucosamine deacetylase from the culture thus obtained.

As described above, the process of the present invention is based on the incubation of a microorganism capable of producing N-acetyl-D-glucosamine deacetylase. Thus the present invention can provide a production technique which harmonizes well with the environment without using any acid or alkali different from the conventional methods. Furthermore, it is not necessary in the process of the present invention to spend much cost and labor for the post-treatment of the acid or alkali as is the case with the conventional methods.

In addition, this microorganism produces a large amount of N-acetyl-D-glucosamine deacetylase. Accordingly, the present invention enables the industrial production of N-acetyl-D-glucosamine deacetylase in a large amount.

DESCRIPTION OF THE PREFERRED EMBODIMENTS

Figure 1:
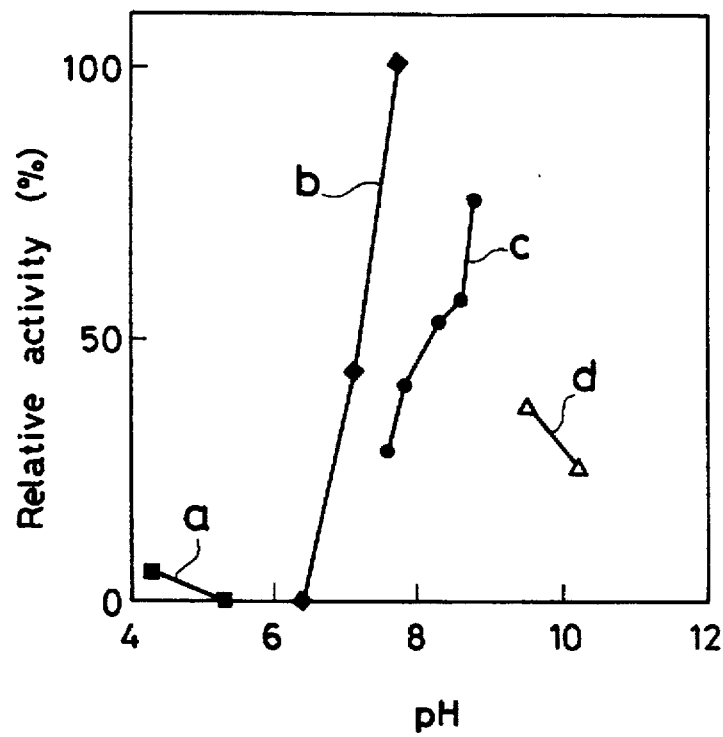
FIG. 1 shows the relationship between the relative activity (%) of N-acetyl-D-glucosamine deacetylase originating in the Alteromonas sp. Mct-9 strain (FERM BP-5369) and the pH value, at 37° C.

The microorganism producing N-acetyl-D-glucosamine deacetylase to be used in the present invention is one which belongs to the genus Alteromonas and has, for example, the following mycological properties. Any microorganism may be used therefor, so long as it belongs to the genus Alteromonas and is capable of producing N-acetyl-D-glucosamine deacetylase. For example, use can be made of a marine bacterium Mct-9 strain (FERM BP-5369) isolated from the deep sea of the area of the Mariana Trough by the present inventors. The marine bacterium Mct-9 strain was deposited, on the basis of Budapest Treaty, to "National Institute of Bioscience and Human-Technology, Agency of Industrial Science and Technology", residing at 1–3, Higashi 1 chome, Tsukuba-shi, Ibaraki-ken 305 Japan, under the accession number FERM BP-5369, on the day of Jan. 23, 1996.

The mycological properties of this marine bacterium Mct-9 strain (FERM BP-5369) are as follows.

1. Morphological property

| | | |
|---|---|---|
| (1) | Cell morphology | curved rod. |
| (2) | Motility | +. |
| (3) | Flagella morphology | polar flagellation. |
| (4) | Gram stain | negative. |

-continued

2. Physiological property

| | | |
|---|---|---|
| (1) | Luminescence | −. |
| (2) | Growth temperature at | |
| | 4° C. | +. |
| | 35° C. | +. |
| | 40° C | +. |
| (3) | Reduction of nitrate | −. |
| (4) | O-F test | oxidative. |
| (5) | Oxidase | +. |
| (6) | Catalase | +. |
| (7) | DNA degradation | −. |
| (8) | Gelatin decomposition | +. |
| (9) | Chitin decomposition | +. |
| (10) | Starch decomposition | −. |
| (11) | Metabolism of carbon compound | |
| | D-mannose | −. |
| | D-fructose | −. |
| | sucrose | +. |
| | maltose | +. |
| | N-acetylglucosamine | +. |
| | succinate | +. |
| | fumarate | +. |
| | citrate | −. |
| | erythritol | −. |
| | glycerol | −. |
| | sorbitol | −. |
| | DL-malate | −. |
| | α-ketoglutarate | −. |
| | m-hydroxybenzoate | −. |
| (12) | Chromogen | −. |
| (13) | Requirement for salt | +. |

3. Intracellular DNA GC content (mol %) 40.
4. Origin:
   seawater in the area of the Mariana Trough
   (depth: ca. 4,000 m).

These mycological properties are examined in accordance mainly with Yoshio Ezura, "Engan Kankyo Chosa Manyuaru II [Suishitsu, Biseibutsu-hen]", ed. by Nippon Kaiyo Gakkai, Koseisha Koseikaku, pp. 356–364 (1990). Also, use is made of Kazuo Komagata, "Biseibutsu no Bunrui to Dotei (II)", (revised, ed. by Takeharu Hasegawa), Gakkai Shuppan Senta, pp. 99–161 (1985) as a reference.

The luminescence is examined by reference to J. L. Reichelt and P. Baumann, Arch. Mikrobiol., 94, 283 (1973). The reduction of nitrate is examined by reference to Φ. Enger et.al., Int. J. Syst. Bacteriol., 37, 416 (1987). The decomposition of starch and the metabolism of carbon compounds are examined by reference to M. Akagawa-Matsushita et al., Int. J. Syst. Bacteriol., 42, 621(1992); P. Baumann et al., J. Bacteriol., 107, 268 (1971); and L. Baumann et al., J. Bacteriol., 110, 402 (1972). The GC content in intracellular DNA is determined by reference to E. Yabuuchi et al., Atarashii Bunruigaku ni Bansosuru Saikin Dotei-ho, Saikon Shuppan, pp. 88–97 (1987).

By reference to Bergey's Manual of Systematic Bacteriology, Vol. 1 (ed. by N. R. Krieg and J. G. Holt, Williams & Wilkins, Baltimore, 1984), these mycological properties are compared with the data given in Bergey's Manual of Determinative Bacteriology (9th ed., Ed. by J. G. Holt, N. R. Krieg, P. H. A. Sneath, J. T. Staley and S. T. Williams, Williams & Wilkins, Baltimore, 1994). As a result, it is found out that the above-mentioned marine bacterium Mct-9 strain (FERM BP-5369) is a bacterium belonging to the genus Alteromonas and similar in a number of properties to *Alteromonas undina*. However, the former strain is different from the latter in the growth at 35° C. (Mct-9: +, *A. undina:* −) and the GC content of intracellular DNA (Mct-9 strain: 40% by mol, *A. undina:* 43–44% by mol).

With the use of this marine bacterium Mct-9 strain (FERM BP-5369), N-acetyl-D-glucosamine deacetylase can be produced by inoculating this strain into an appropriate medium and incubating the same by a conventional method preferably in the presence of an inducer. As the inducer, use can be made of chitin, decomposition products of chitin, N-acetyl-D-glucosamine or N-acetyl-D-glucosamine oligomers either alone or combinedly. Preferable examples of the inducer include N-acetyl-D-glucosamine and N-acetyl-D-glucosamine oligomers. It is the most desirable to use N-acetyl-D-glucosamine as the inducer. The inducer is added to give a concentration of at least 0.1 g/l, preferably from 1.0 to 50 g/l. As the medium, any publicly known one may be used. For example, use can be made of glucose, maltose, xylose, sucrose, peptone, etc. as the carbon source. As the nitrogen source, use can be made of organonitrogen materials such as yeast extract, peptone, meat extract and amino acid solutions and inorganic nitrogen compounds such as ammonium sulfate and ammonium chloride. It is also possible to use the inducer as the carbon source or the nitrogen source. As the inorganic salts, use can be made of magnesium sulfate, magnesium chloride, sodium phosphate, potassium phosphate, potassium chloride, sodium chloride, calcium chloride, etc. appropriately combined with each other. The pH value of the above-mentioned medium is regulated within a range of from 6.5 to 8.0 by adding an appropriate acid or base. The medium is sterilized in an autoclave. The incubation is effected at a temperature ranging from 2° to 35° C., preferably from 10° to 22° C., for 12 to 48 hours under aeration/stirring or shaking. By using a plate medium optionally containing the above-mentioned carbon source, nitrogen source, inorganic salts and agar, the incubation is effected at a temperature of from 2° to 35° C., preferably from 10° to 22° C., for 15 to 72 hours. Alternatively, this strain can be incubated statically.

From the culture thus obtained, the medium may be separated from the cells by a method commonly employed in the art such as centrifugation or filtration. Centrifugation is appropriately employed therefor. The enzyme accumulated in the cells may be extracted by a method commonly employed in the art, for example, ultrasonic cell disruption, cell disruption with the use of a Dynomill cell disrupter wherein the culture is rotated together with glass beads, or destruction of cell membrane with the use of enzymes (lysozyme, etc.) or organic solvents (toluene, etc.). The enzyme can be recovered by extracting the cells with the use of an appropriate method selected from among those described above.

The N-acetyl-D-glucosamine deacetylase may be further purified, if necessary, from the crude enzyme solution thus extracted by appropriately combining means commonly employed for purifying enzymes, for example, ammonium sulfate precipitation, ion exchange column chromatography, gel filtration, adsorption chromatography, hydrophobic chromatography and preparative electrophoresis.

The N-acetyl-D-glucosamine deacetylase obtained by the process of the present invention has the following physico-chemical properties.

(1) Action: acting on the acetamido Group of N-acetyl-D-Glucosamine to thereby form D-Glucosamine.

(2) Substrate specificity: acting on N-acetyl-D-Glucosamine but not on N-acetyl-D-Glucosamine oligomers.

(3) Optimum pH value: 7.8–8.0 (shown in FIG. 1).

In FIG. 1, a stands for a 40 mM acetic acid/sodium acetate buffer solution containing N-acetyl-D-Glucosamine deacetylase; b stands for a 40 mM potassium dihydrogenphosphate/sodium dihydrogenphosphate buffer solution containing N-acetyl-D-Glucosamine deacetylase; c stands for a 40 mM boric acid/potassium chloride/sodium hydroxide buffer solution containing N-acetyl-D-Glucosamine deacetylase; and d stands for a 40 mM sodium hydrogencarbonate/sodium hydroxide buffer solution containing N-acetyl-D-glucosamine deacetylase. As FIG. 1 indicates, the 40 mM potassium dihydrogenphosphate/sodium dihydrogenphosphate buffer solution shows a sharp change in relative activity (%) and the highest level of the relative activity (%) at pH 7.8 to 8.0. It is therefore advantageous to use a 40 mM potassium dihydrogenphosphate/sodium dihydrogenphosphate buffer solution as the buffer solution.

(4) Stable pH value: 6.0–8.0 (after incubating at 37° C. for 30 minutes, at least 70% of the activity is sustained).

(5) Optimum temperature: 48° C. (shown in FIG. 2).

Figure 2:
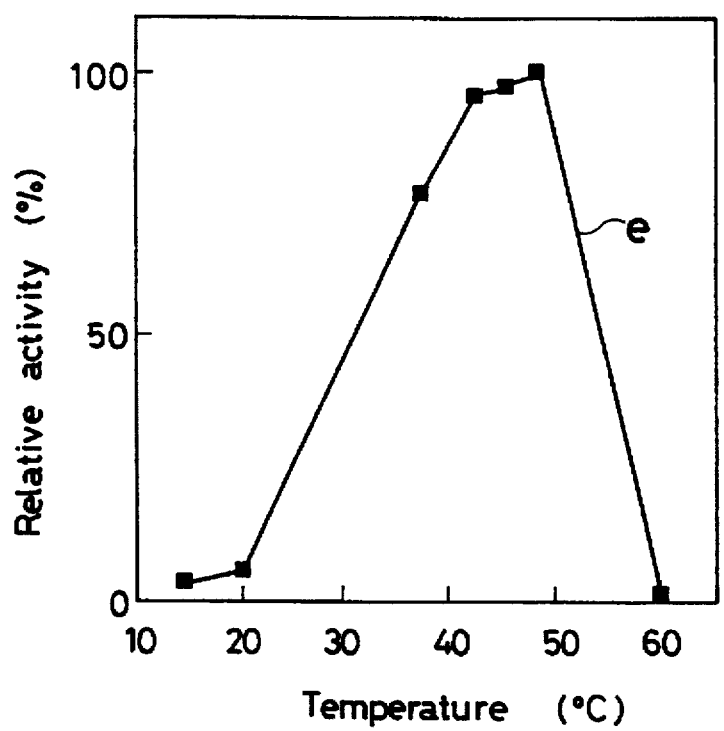
FIG. 2 shows the relationship between the relative activity (%) of N-acetyl-D-glucosamine deacetylase originating in the Alteromonas sp. Mct-9 strain (FERM BP-5369) contained in a buffer solution, and the temperature (° C.), at pH 7.8.

In FIG. 2, e stands for a 40 mM acetic acid/sodium acetate buffer solution containing N-acetyl-D-glucosamine deacetylase. As FIG. 2 shows, the relative activity (%) attains the highest level at a temperature of 48° C.

(6) Heat stability: 43° C. (after incubating at pH 7.8 for 30 minutes, at least 70% of the activity is sustained).

The activity is determined by the following method. Namely, 0.3 ml of a 10% solution of N-acetyl-D-glucosamine is added as a substrate to 0.1 ml of a 200 mM phosphate buffer solution (pH 7.8). Next, 0.1 ml of an enzyme solution is further added thereto followed by incubation at 48° C. for 30 minutes. Then the D-glucosamine thus formed is determined by the indole/hydrochloric acid colorimetry. The amount of the enzyme by which 1 μmol of D-glucosamine is formed in a minute is referred to as 1 U (unit).

To further illustrate the present invention in greater detail, the following Example will be given.

EXAMPLE

Alteromonas sp. Mct-9 strain (FERM BP-5369) was inoculated into a plate medium (pH 7.4) containing, per 200 ml of the medium, 0.6 g of ammonium nitrate, 0.2 g of dipotassium hydrogenphosphate, 2 g of sodium chloride, 0.12 g of magnesium sulfate, 0.02 g of calcium chloride, 10 g of glucose and 3 g of agar and incubated therein at 20° C. for 48 hours. Next, the cells were collected with a sterilized spatula and inoculated into a liquid medium (pH 7.4) which had been prepared by adding 25 g of N-acetyl-D-glucosamine (i.e., the inducer for the enzyme) to 500 ml of a commercially available solution of Marine broth (mfd. by Difco). After mixing, the cells were incubated at 20° C. for 24 hours while shaking under aerobic conditions.

Subsequently, the medium was centrifuged at 10,000×g for 15 minutes to thereby give 20 g of wet cells. The cells thus obtained were suspended in 40 ml of physiological saline. After effecting ultrasonication at 0° C. for 10 minutes (each cycle consisting of the operation for 20 seconds and rest for 20 seconds), the suspension was centrifuged (16,000×g, 1 hour) to thereby give the supernatant. The total activity of N-acetyl-D-glucosamine deacetylase in this supernatant was 12.6 U, while the specific activity thereof was 0.0063 U/mg-protein.

This supernatant was passed through 35 ml of a DEAE Bio-Gel A column (mfd. by Bio-Rad) preliminarily equilibrated with a 10 mM phosphate buffer solution (pH 7.0) and thus the target enzyme was adsorbed thereby. After washing with the same phosphate buffer solution, the column was eluted while changing the concentration of sodium chloride stepwise to thereby give N-acetyl-D-glucosamine deacetylase having a total activity of 10.7 U and a specific activity of 0.069 U/mg-protein.

The activity of N-acetyl-D-glucosamine deacetylase was determined on various substrates [i.e., N-acetyl-D-glucosamine and N-acetyl-D-glucosamine oligomers (dimer to hexamer)]. As a result, this enzyme was found to act exclusively on N-acetyl-D-glucosamine.

As discussed above, the present invention provides a technique by which N-acetyl-D-glucosamine deacetylase can be easily produced in a pure state without using chemicals such as alkalis or acids which require much cost or labor for the post-treatment as is the case with the conventional methods. The present invention furthermore provides a technique for industrially producing N-acetyl-D-glucosamine deacetylase.

What is claimed is:

1. A process for producing N-acetyl-D-glucosamine deacetylase comprising incubating a microorganism which is a marine bacterium Alteromonas Mct-9 strain (FERM BP-5369) and is capable of producing N-acetyl-D-glucosamine deacetylase and recovering N-acetyl-D-glucosamine deacetylase from the culture thus obtained.

* * * * *